United States Patent [19]

Weisshaupt

[11] Patent Number: 5,722,988

[45] Date of Patent: Mar. 3, 1998

[54] SURGICAL TUBULAR-SHAFTED INSTRUMENT

[76] Inventor: Dieter Weisshaupt, Johann-Peter-Hebel-Strasse 15, D-78194 Immendingen, Germany

[21] Appl. No.: 661,397

[22] Filed: Jun. 7, 1996

Related U.S. Application Data

[63] Continuation of PCT/EP94/03381, Oct. 13, 1994.

[30] Foreign Application Priority Data

Dec. 8, 1993 [DE] Germany .................. 43 41 735.3

[51] Int. Cl.$^6$ .................................................. A61B 17/28
[52] U.S. Cl. .................................. 606/205; 606/206
[58] Field of Search ............................ 606/205, 206, 606/207, 208, 170

[56] References Cited

U.S. PATENT DOCUMENTS

| | | | |
|---|---|---|---|
| 5,496,347 | 3/1996 | Hashiguchi et al. | 606/205 |
| 5,618,308 | 4/1997 | Holmes et al. | 606/205 |

FOREIGN PATENT DOCUMENTS

| | | |
|---|---|---|
| 0 225 045 A1 | 6/1987 | European Pat. Off. . |
| 0 541 930 A1 | 5/1993 | European Pat. Off. . |
| 0 546 767 A2 | 6/1993 | European Pat. Off. . |
| 91 05 399.4 | 10/1991 | Germany . |
| 91 14 306.3 | 3/1992 | Germany . |
| 93 17 535.3 | 3/1994 | Germany . |
| WO 91/02493 | 3/1991 | WIPO . |

OTHER PUBLICATIONS

Company Brochure entitled, "Introducing Nu-Tip: scissor instrumentation that's both disposable and reusable", Marlow Surgical Technologies, Inc.

*Primary Examiner*—Michael Buiz
*Assistant Examiner*—Kevin Truong
*Attorney, Agent, or Firm*—Barry R. Lipsitz; Ralph F. Hoppin

[57] ABSTRACT

A tool is secured to a tube of a tubular-handled surgical instrument via a tool holder. An actuator is fitted in the tube and is movable longitudinally therein to move the tool. The tool holder has an extension which can be inserted into the tube. At its end surrounding the extension, the tube has radially movable components which, when pushed in, secure the extension by a frictional or force fit against axial movement in the tube. When radially pulled out, the fit is broken and the extension can be axially extracted from the tube.

21 Claims, 3 Drawing Sheets

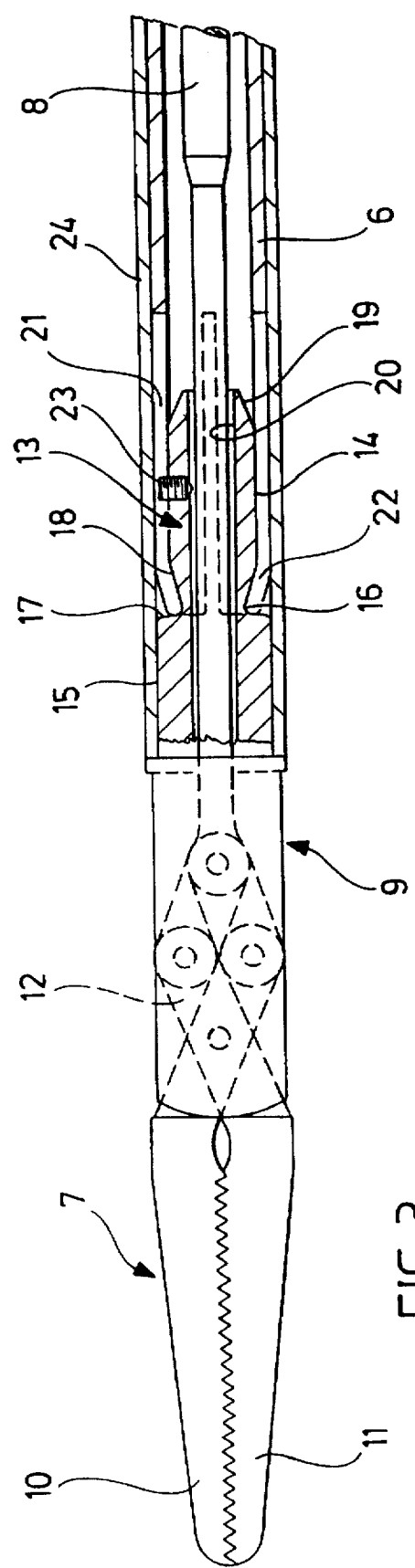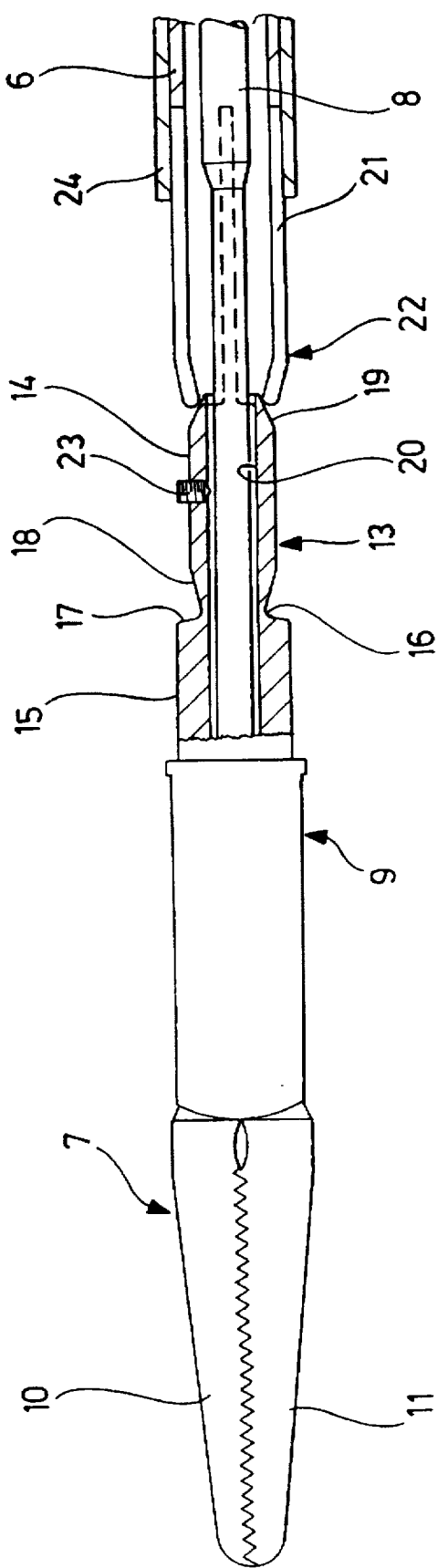

SURGICAL TUBULAR-SHAFTED INSTRUMENT

This application is a continuation of International PCT Application No. PCT/EP94/03381, filed on Oct. 13, 1994.

BACKGROUND OF THE INVENTION

The invention relates to a surgical tubular-shafted instrument comprising a tube, at the end of which a holder for a tool is detachably held, and an actuating element arranged in the tube and movable longitudinally therein for moving the tool, wherein the holder bears an extension insertable into the tube and wherein the tube has radially displaceable parts at its end surrounding the extension, these parts securing the extension against axial displacement in the tube in the inserted state as a result of positive or frictional locking but terminating the engagement in the radially withdrawn state and facilitating an axial removal of the extension out of the tube.

Surgical tubular-shafted instruments of this type are used for the most varied of purposes for cutting, securing, coagulating etc. Normally, a separate instrument is required for each application but it is also known to arrange the tools detachably on the tube of the instrument. For this purpose, the tool holders can, for example, be designed to be screwed into the tube while, at the same time, a separation of the actuating element takes place in the end region of the tube (company brochure of Marlow Surgical Technologies Inc. "Nu-Tip").

Such a connection of the tool holder with the tube is relatively complicated, in particular it is necessary, in certain circumstances, to exert relatively large forces on tool and tube when these are being screwed together or apart; moreover, the thread requires a certain wall thickness of the tube which can possibly be a hindrance in view of the ever increasing miniaturization of the instruments.

EP 0 225 045 A1 discloses a surgical tubular-shafted instrument of the type described at the outset, with which the holder of the tool is secured solely by way of radially resilient spring fingers of a sheath which is part of the tubular shaft. The holder is detached from the sheath by pulling it powerfully out of this sheath and the spring fingers thereby spring outwards. There is, however, the risk that such a detachment could be caused unintentionally. To avoid this, the spring fingers must be of a very strong design. On the other hand, it is necessary for this purpose to exert considerable forces on the holder when it is intended to be detached from the tubular shaft. Since the tubular-shafted instruments as described are very sensitive instruments of small dimensions, this results in the risk of damage.

The object of the invention is to design a tubular-shafted instrument of the generic type such that the holder can be detached from the tubular shaft with small forces, that, however, the holder is still securely held in the tubular shaft in axial direction and cannot be detached unintentionally.

SUMMARY OF THE INVENTION

This object is accomplished in accordance with the invention, in a tubular-shafted instrument of the type described at the outset, in that an outer tube is mounted on the tube for longitudinal displacement, this outer tube securing tube and extension in positive or frictional locking when pushed over the region of engagement of the extension in the tube but facilitating the radial withdrawal of the tube when pushed away from this region. As a result, it is possible to obtain a faultless axial fixing in position with a design of the tube which is relatively economical with respect to material and, therefore, weak since the radial forces for maintaining the positive or frictional locking are absorbed by the outer tube which is longitudinally displaceable on the tube and surrounds it.

Particularly advantageous is a design, in which the tube bears at its end tongues which are angled inwardly and separated from one another by longitudinal slots in the tube casing and which, in the inserted state, engage with their inwardly angled ends in recesses on the circumference of the extension. With this solution it is sufficient to divide the tube into tongues at its end by means of longitudinal slots and to bend these inwards at their free ends in order to already achieve a connection possibility in this way. During the insertion of the extension, the tongues are bent elastically outwards and subsequently lock into the recesses of the extension with their inwardly angled ends so that any axial displacement is prevented.

In this respect, it is favorable when the recesses are formed by a circumferential annular groove in the extension.

It is, furthermore, particularly advantageous when the extension is designed in a circular-cylindrical shape, rests with its outer casing areally against the inner side of the tube and bears the circumferential annular groove at a distance from its free end. This results in a perfect mounting of the holder in the interior of the tube; the fact that the circular-cylindrical outer casing of the extension rests against the inner side of the tube over a certain longitudinal region results in a flawless guidance of the extension in the tube and a distribution of the forces to be absorbed over a greater longitudinal region.

In the preferred embodiment, the annular groove can be designed in cross section in the shape of a saw tooth, the steep flank facing away from the free end of the extension. During the insertion of the extension, the inwardly angled, free ends of the elastic tongues of the tube thereby slide into the annular groove and abut on the steep flank, whereby the depth of insertion is limited. During removal, the inwardly angled ends of the tongues slide along the flat flank and therefore make it possible for the extension to be drawn out of the tube without any problem.

It can, in addition, be provided for the extension to bear at its free end a diverging slide-on surface merging into the circular-cylindrical region. This facilitates the insertion of the extension into the tube and the resulting elastic bending open of the tongue-shaped tube regions.

In this respect it is advantageous when the outer tube can be pushed over a cylindrical region of the extension which adjoins the region of engagement of the extension dipping into the tube and rests against the inner wall of the outer tube. This results in a frictional connection between extension and outer tube which contributes to stabilizing the entire instrument since the outer tube also rests areally on the tube accommodating the extension. The outer tube therefore undertakes an additional reinforcing function between extension, on the one hand, and tube, on the other hand.

In a particularly preferred embodiment it is provided for the outer tube to consist of an electrically insulating material. This makes it possible to use the parts arranged within the outer tube as electrical conductors, for example in the case of instruments which are used for electrocoagulation. Nevertheless, the surrounding body tissue is reliably protected from the voltage-carrying inner parts of the instrument. The outer tube therefore undertakes an additional function, namely to electrically insulate the tube and the parts located therein in relation to the surroundings.

3

In this respect, it is advantageous when a reinforcement sleeve is inserted into the outer tube, which consists, for example, of a plastic material, in its end section covering the extension. Due to this reinforcement sleeve, the necessary mechanical strength can, therefore, be achieved in this region which is particularly subject to mechanical loads although the plastic material largely retains the electrical insulation properties.

The reinforcement sleeve preferably consists of metal.

It can be arranged, in particular, on the inner side of the outer tube and merge steplessly into the adjoining section of the outer tube. This does not result in any difficulties whatsoever when the outer tube is pushed onto the tube and the extension.

It is, furthermore, advantageous when the holder is coated on its outer side with an electrically insulating material which extends right up to the region covered by the outer tube. In the region of the tool itself, this also results in an electrical insulation in relation to the surroundings which extends over the entire length of the instrument.

In a preferred embodiment, the tube and the extension are secured relative to one another against any turning about the longitudinal axis of the tube by positive engagement of projections and recesses. It can, in particular, be provided for the extension to bear at least one radially protruding projection which engages in longitudinal slots in the tube which are open towards the end of the tube.

This results in the possibility of designing the connection between tool holder, on the one hand, and tube, on the other hand, such that attention need be paid only to the securing in position axially but not to the securing against rotation. This is undertaken by the special rotational securing means. This simplifies the design of the connection between tool holder, on the one hand, and tube, on the other hand. Moreover, in comparison with a connection by means of a screw-in thread this solution results in the certainty of preventing any rotation. When using screw-in threads it cannot be ruled out that the screw connection will be released unintentionally during operation due to large torques which occur. This risk does not apply with the new construction described.

The following description of preferred embodiments of the invention serves to explain the invention in greater detail in conjunction with the drawings.

BRIEF DESCRIPTION OF THE DRAWINGS

FIG. 2: is a partially cutaway side view of the front part in the preferred embodiment of a tubular-shafted instrument with a tool secured on the tube;

FIG. 3: is a view similar to FIG. 2 with a tool detached from the tube and

DETAILED DESCRIPTION OF THE INVENTION

Figure 1:
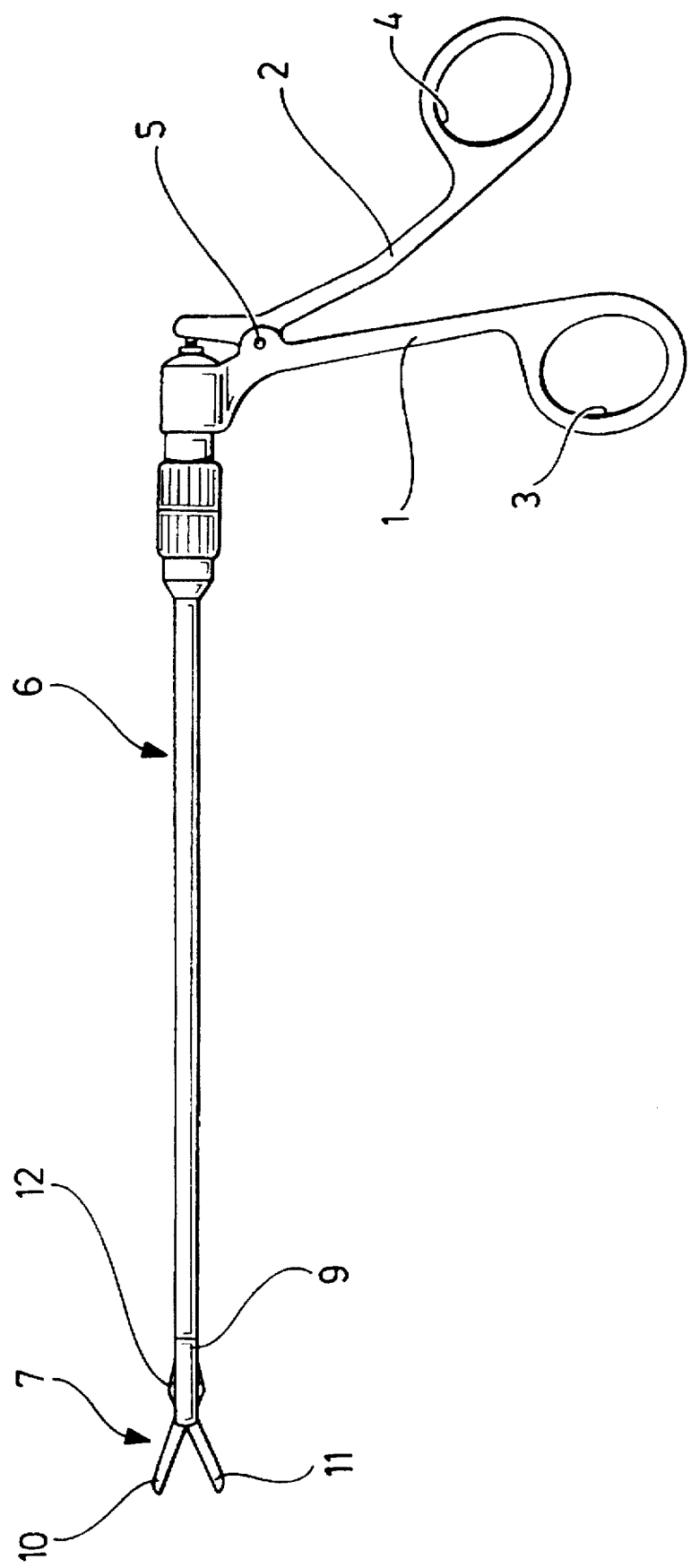
FIG. 1: is a schematic side view of a tubular-shafted instrument.

The surgical tubular-shafted instrument is described in the following on the basis of the example of an instrument which can be actuated with two gripping arms pivotable relative to one another. It goes without saying that any type of instrument, with which an actuating element which actuates a tool at the end of a tube is mounted for displacement in the tube, is covered by the invention. The actuating element can also be driven in a manner other than by way of gripping arms pivotable relative to one another, for example by direct displacement of the actuating element or by special motor drive means.

The tubular-shafted instrument displayed in the drawings comprises two gripping arms 1, 2 mounted so as to be pivotable relative to one another and each having a finger opening 3 and 4, respectively, these arms being pivotally connected with one another at a bearing point 5.

One of the gripping arms 1 bears an elongated tube 6, at the free end of which a tool 7 is held which can be designed, for example, as forceps or scissors.

An actuating element in the form of a push and pull rod 8 is arranged in the interior of the tube 6 and this rod is connected via swivel connections, on the one hand, to the tool 7 and, on the other hand, to the other gripping arm 2. By opening and closing the gripping arms 1 and 2, the push and pull rod 8 is longitudinally displaced in the tube 6 and thereby actuates the tool 7.

The construction of the tubular-shafted instrument in the region of the transitional point between the tube 6, on the one hand, and the tool 7, on the other hand, will be explained in greater detail on the basis of FIGS. 2 to 4.

The tool 7 comprises a holder 9, on which movable parts 10, 11 of the tool are rotatably mounted. Moreover, the holder 9 accommodates gear means 12 which are rotatably connected with the push and pull rod 8 and which translate a movement of the push and pull rod into a rotary movement of the parts 10 and 11.

The holder 9 merges at its side facing the tube 6 into a stepped, circular-cylindrical extension 13 which has a section 14 with a smaller external diameter adjacent the end of the extension 13 and a section 15 with a larger external diameter adjoining thereto. In the region of transition between the two sections 14 and 15 a circumferential groove 16, which is formed by a conical shape of the casing surface of the section 14, is located in the extension 13. This gives the circumferential groove 16 the cross section of a saw tooth with a steep flank 17 formed by the step between the sections 14 and 15 and with a flat flank 18 merging into the cylinder surface of the section 14.

A conical slide-on surface 19 is formed at the free end of the extension 13 and this surface likewise merges into the cylinder surface of the section 14. The extension 13 accommodates a central bore 20, in which the push and pull rod 8 is arranged so as to extend as far as the gear parts 12. This push and pull rod 8 can be a continuous bar; in the illustrated embodiment it is formed in two parts and widens in the interior of the tube 6; this is not absolutely necessary.

The tube 6 is divided at its free end by a plurality of longitudinal slots 21 into tongue-shaped wall regions 22 which are angled slightly radially inwards at the free end of the tube 6. The angling of these tongue-shaped wall regions 22 corresponds essentially to the angle of the flat flank 18 of the circumferential groove 16; in addition, the length of the angled region is selected such that the angled part of the tongue-shaped wall region 22 is approximately equal in length to the flat flank 18 of the circumferential groove 16. The external diameter of the section 14 corresponds to the internal diameter of the tube 6. A screw 23, which protrudes slightly beyond the external diameter of the section 14 and the diameter of which corresponds to the width of the longitudinal slots 21 in the tube 6, is inserted into the section 14 in radial direction.

An outer tube 24 is arranged on the tube 6 for longitudinal displacement and its internal diameter corresponds to the external diameter of the tube. This internal diameter corresponds, in addition, to the external diameter of the section 15 of the extension.

Figure 4:
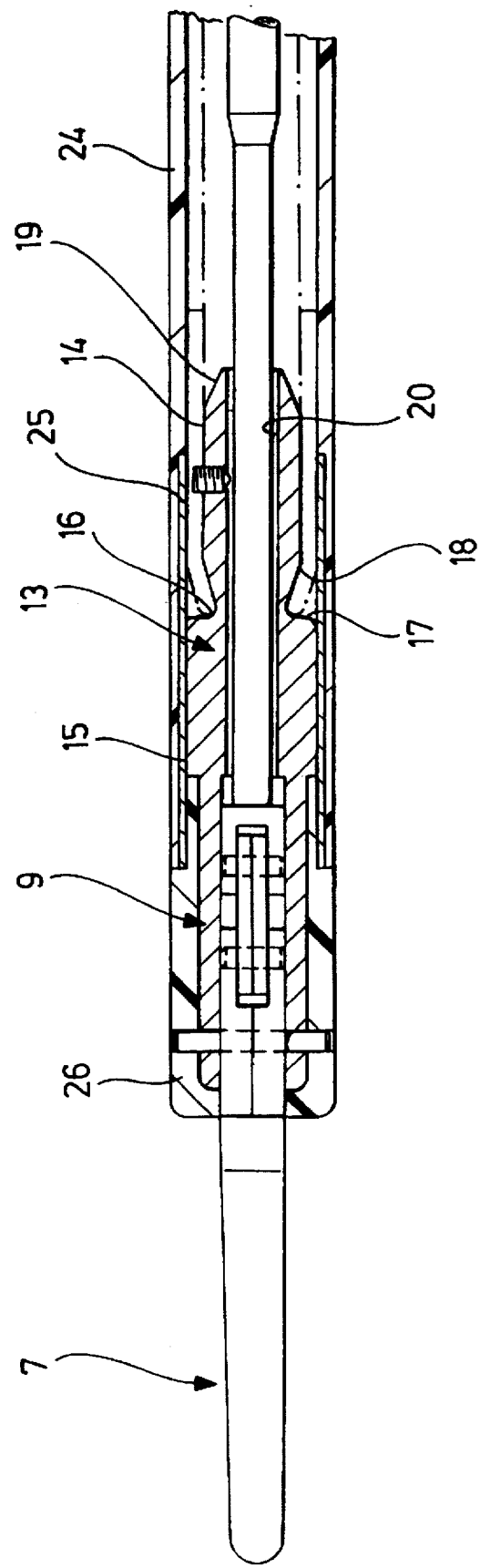
FIG. 4 is an enlarged view of the front part of an additional, preferred embodiment of a tubular-shafted instrument with electrical insulation (without a tool).

This outer tube can consist of metal in accordance with the illustration in FIGS. 2 and 3 but it is favorable when this outer tube 24 consists of an electrically insulating material, for example of plastic, in accordance with the embodiment in FIG. 4. In this case, a reinforcement sleeve 25 (FIG. 4), which can consist, for example, of metal, is set into the region of the outer tube 24 near its end. The reinforcement sleeve 25 is preferably arranged at the inner side of the outer tube 24 and fitted such that the inner wall of the outer tube 24 is stepless. In an embodiment with an outer tube consisting of electrically insulating material, it is, in addition, advantageous when the holder 9 is coated on the outside with an electrically insulating material 26, for example likewise with plastic. This preferably extends right into the section 15 of the extension 13 so that the electrically insulating outer tube 24 can adjoin directly onto this electrically insulating material 26, partially even covering it.

When connecting a tool 7 with a tube 6, the outer tube 24 displaceably mounted on the tube 6 is first of all pushed back in relation to the tube 6 to such an extent that the tongue-shaped wall regions 22 of the tube 6 are exposed and can therefore be bent elastically outwards. A tool 7 is brought towards the tube 6 in the manner illustrated in FIG. 3 such that the slide-on surface 19 of the extension 13 abuts on the free ends of the tongue-shaped wall regions 22 and thereby pushes these elastically and radially outwards. When the section 14 is inserted further into the tube 6, the tongue-shaped wall regions 22 slide along its outer surface until the angled parts of the tongue-shaped wall regions 22 reach into the circumferential groove 16. The displacing movement is limited by abutment of the tongue-shaped wall regions 22 on the steep flank 17. When this position is reached, the tongue-shaped wall regions 22 rest with their cylindrical part areally on the cylindrical casing surface of the section 14 whereas the angled parts of the tongue-shaped wall regions 22 engage in the circumferential groove 16, preferably abutting areally on the flat flank 18, as illustrated in FIG. 2. The extension is thereby secured against any rotation in relation to the tube 6 by the engagement of the screw 23 in one of the longitudinal slots 21. To permanently fix this connection, the outer tube 24 is subsequently pushed over the tube 6 to such an extent that the tongue-shaped wall regions 22 are secured in position in radial direction, i.e. they can no longer move radially outwards. The outer tube 24 is thereby pushed completely over the section 15 of the extension 13 so that a reinforcement in the connection region results from this. Holder 9 and tube 6 are thus secured so as to be non-displaceable in axial direction; furthermore, a connection between holder 9 and the tube 6 which is resistant to bending also results due to the coaxial engagement in one another of the tube 6, the outer tube 24 and the extension 13.

This connection can be released again in the simplest manner when the outer tube 24 is drawn back and the tongue-shaped wall regions 22 again exposed. It is then possible to withdraw the tool 7 out of the tube 6, the push and pull rod 8 also being drawn out.

In the embodiment of FIG. 4, a complete, electrically insulating encasement of the entire shaft portion of the instrument results in the assembled state with the outer tube 24 pushed forward and so this instrument can be used for electrical treatment procedures.

What is claimed is:

1. A surgical tubular-shafted instrument, comprising:

a first tube having a free end which is adapted to detachably hold a holder for a tool;

said holder comprising an extension which is insertable into said free end;

an actuating element for moving the tool, said actuating element extending in the first tube and being movable axially therein; and an outer tube which surrounds said first tube and is longitudinally positionable between a closed position and an open position;

said first tube comprising radially displaceable parts at said free end; wherein:

said parts are adapted to surround the extension and secure the extension against axial displacement in the first tube when said extension is inserted into said free end;

said outer tube is adapted to secure said extension against axial displacement in the first tube when said extension is inserted into said free end and said outer tube is in said closed position over said extension by preventing radially outward displacement of said parts; and said parts and said outer tube facilitate an axial removal of the extension from said first tube when said outer tube is positioned in said open position away from said free end.

2. An instrument as defined in claim 1, wherein:

said parts comprise tongues with inwardly angled ends, said tongues being separated from one another by longitudinal slots in said first tube;

said inwardly angled ends being adapted to engage in recesses on a circumference of the extension.

3. An instrument as defined in claim 2, wherein:

the outer tube is adapted to be pushed over a cylindrical region of the extension which adjoins a region of the extension which is surrounded by said parts when said extension is inserted into said free end of said first tube;

said cylindrical region of the extension being adapted to dip into the outer tube and rest against an inner wall of the outer tube.

4. An instrument as defined in claim 2, wherein:

the outer tube comprises an electrically insulating material.

5. An instrument as defined in claim 4, wherein:

a reinforcement sleeve is provided at an end section of the outer tube and is adapted to cover the extension, at least in part, when said extension is inserted into said free end of said first tube and said outer tube is in said closed position.

6. An instrument as defined in claim 5, wherein:

the reinforcement sleeve comprises metal.

7. An instrument as defined in claim 4, wherein:

an outer side of the holder is coated with an electrically insulating material which extends into a region of said holder which is covered by the outer tube when said extension is inserted into said free end of said first tube and said outer tube is in said closed position.

8. An instrument as defined in claim 2, wherein:

the recesses are formed by a circumferential annular groove in the extension.

9. An instrument as defined in claim 8, wherein:

the extension comprises an outer casing having a circular-cylindrical region which is disposed between said circumferential annular groove and a free end of the extension; and said outer casing is adapted to rest areally against an inner side of the first tube when said extension is inserted into said free end of said first tube.

10. An instrument as defined in claim 9, wherein:

the circumferential annular groove is designed in cross section in the shape of a saw tooth, said saw tooth having a steep flank facing away from the free end of the extension.

11. An instrument as defined in claim 9, wherein:

the extension comprises at its free end a diverging slide-on surface merging into the circular-cylindrical region.

12. An instrument as defined in claim 9, wherein:

the outer tube is adapted to be pushed over a cylindrical region of the extension which adjoins a region of the extension which is surrounded by said parts when said extension is inserted into said free end of said first tube;

said cylindrical region of the extension being adapted to dip into the outer tube and rest against an inner wall of the outer tube.

13. An instrument as defined in claim 9, wherein:

the outer tube comprises an electrically insulating material.

14. An instrument as defined in claim 1, wherein:

the outer tube is adapted to be pushed over a cylindrical region of the extension which adjoins a region of the extension which is surrounded by said parts when said extension is inserted into said free end of said first tube;

said cylindrical region of the extension being adapted to dip into the outer tube and rest against an inner wall of the outer tube.

15. An instrument as defined in claim 1, wherein:

the outer tube comprises an electrically insulating material.

16. An instrument as defined in claim 15, wherein:

a reinforcement sleeve is provided at an end section of the outer tube and is adapted to cover the extension, at least in part, when said extension is inserted into said free end of said first tube and said outer tube is in said closed position.

17. An instrument as defined in claim 16, wherein:

the reinforcement sleeve comprises metal.

18. An instrument as defined in claim 16, wherein:

the reinforcement sleeve is arranged on an inner side of the outer tube and merges steplessly into an adjoining section of the outer tube.

19. An instrument as defined in claim 15, wherein:

an outer side of the holder is coated with an electrically insulating material which extends into a region of said holder which is covered by the outer tube when said extension is inserted into said free end of said first tube and said outer tube is in said closed position.

20. An instrument as defined in claim 1, wherein:

said first tube and said extension are secured relative to one another against rotation about a longitudinal axis of the first tube by positive engagement of projections and recesses.

21. An instrument as defined in claim 20, wherein:

the extension comprises at least one radially protruding projection which is adapted to engage in longitudinal slots in the first tube to prevent said rotation;

said slots being open towards the free end of the first tube.

\* \* \* \* \*